United States Patent [19]

Okpanyi et al.

[11] Patent Number: 5,376,372
[45] Date of Patent: Dec. 27, 1994

[54] ANALGESIC AND INFLAMMATION-REDUCING MEDICAMENT

[75] Inventors: Samuel N. Okpanyi, Wiesbaden; Michaela Arens-Corell, Bischofsheim, both of Germany

[73] Assignee: Steigerwald Arzneimittelwerk GmbH, Darmstradt, Germany

[21] Appl. No.: 26,176

[22] Filed: Mar. 1, 1993

Related U.S. Application Data

[63] Continuation of Ser. No. 655,468, Mar. 27, 1991, abandoned.

[30] Foreign Application Priority Data

Jul. 11, 1989 [EP] European Pat. Off. ........ 89112639.3

[51] Int. Cl.$^5$ .............................................. A61K 35/78
[52] U.S. Cl. .................................. 424/195.1; 514/885
[58] Field of Search ...................... 424/195.1; 514/825

[56] References Cited

PUBLICATIONS

J. Metzner, et al. Chem. Abst. 102: 125230f, 1985.
H. Jacker, et al Chem. Abst. 97: 207945k, 1982.
S. Okpanyi, et al. Arzneim–Forsch/Drug Res. 39(I): 698–703, 1989.

Primary Examiner—John W. Rollins
Assistant Examiner—Howard C. Lee
Attorney, Agent, or Firm—Nikaido, Marmelstein, Murray & Oram

[57] ABSTRACT

The use of the medicament having analgesic and inflammation-inhibiting action on a plant basis and containing the constituents
*Populus tremula*
*Solidago virgaurea*
*Fraxinus excelsior*
as the sole carrier of the activity as a basic therapeutic is described.

11 Claims, No Drawings

ANALGESIC AND INFLAMMATION-REDUCING MEDICAMENT

This application is a continuation of application Ser. No. 07/655,468 filed Mar. 27, 1991, abandoned.

The invention relates to an analgesic and inflammation-inhibiting medicament.

In the therapy of inflammatory rheumatological diseases, in particular rheumatoid arthritis, two different medicinal principles are used side by side. The first consists in the reduction of the pain and the inflammatory symptoms in the Joint concerned. Various classes of substance, for example salicylic acid derivatives, acetic and propionic acid derivatives or oxicams are used for this purpose. A summarising expression is "non-steroidal antirheumatics"(NSAR). Their activity is evaluated in the Joint concerned itself. The effects occur rapidly (hours to days). The dose is suited to the immediate situation. A change in course of the inflammatory rheumatic disease does not occur as a result of these medicaments.

The medicament purely on a plane basis described in the WIPO document (WO 87/02248) likewise has the effects of the non-steroidal antirheumatics (NSAR) together with better tolerability.

In addition to the activity described, agents are known and are intensively additionally sought, which favourably influence the entire course of incurable chronic diseases (so-called disease-modifying drugs). They influence pain and inflammation only after long administration (over a period of months) with maintenance doses and are afflicted with considerable side effects (about a third of the patients have to discontinue this treatment). Their activity is initially recognised in an improvement in the signs of systemic inflammation. This is in particular an improvement in the erythrocyte sedimentation test, which is generally used as a method for the assessment of an inflammatory event. Other tests, which, in principle, give no other evidence, are, for example, C-reactive protein (CPR). The long-term aim in this treatment is the reduction or avoidance of joint destruction by rheumatic inflammation. This therapy is familiar today under the name basic therapy.

Because of frequent and occasionally critical side effects, there are carefully worked out rules for treatment with basic therapeutics. For example, results from a 20-week double blind study should be quoted for the change in the erythrocyte sedimentation test (Ward, J. R. et al., Arthritis and Rheumatism Vol. 26, No. 11, 1983, pages 1303–1315).

| Medicament | ESR before therapy | ESR after 20 weeks |
|---|---|---|
| Placebo | 55 | 51 |
| Auranofin | 63 | 22 |
| Gold Na thiomalate | 58 | 33 |

ESR = Erythrocyte sedimentation rate in min/h only for the first hour

Surprisingly, it has now been found in an investigation in various research centres that basic therapeutic effects were also achieved using the medicament disclosed in WO 87/02248. The medicament disclosed in WO 87/02248 was made using the following aqueous ethanolic extracts:

| Populus tremula | 47% by volume of ethanol |
|---|---|
| Fraxinus excelsior | 50% by volume of ethanol |
| Solidago virgaurea | 43% by volume of ethanol |

The individual extracts were prepared from fresh plants and thus the alcohol concentration can vary by ±2.0%.

This medicament having analgesic and inflammation-inhibiting action on a plant basis is distinguished by the constituents Populus tremula, Solidago virgaurea and Fraxinus excelsior as the sole carriers of the activity.

It has proved advantageous if the medicament according to the invention contains 50–70 vol.-% of Populus tremula, 10–30 vol.-% of Solidago virgaurea and 10–30 vol.-% of Fraxinus excelsior.

A particularly preferred composition of the medicament according to the invention contains about 60 vol.-% of Populus tremula, 20 vol.-% of Solidago virgaurea and 20 vol.-% of Fraxinus excelsior.

It is finally in the scope of the invention that bark and leaves are present in the ratio 1:2 in the constituent Populus tremula.

The present invention consists in the surprising discovery that this medicament can be employed not only for the immediate treatment of rheumatic diseases, but rather, in particular, also as a basic therapeutic.

As an example of the basic therapeutic action of the medicament identified according to the invention, results of investigations in the rheumatological department of a hospital are reproduced, in particular by means of the CRP values of the medicament according to WO 87/02248. A clear reduction in these values is shown. It can be safely said that owing to the administration of the medicament of WO 87/02248, the inflammatory activity of the rheumnatological diseases—expressed by C-reactive protein—was clearly lowered. Some results are given below in tabular form:

| Time interval | CRP Values Average value | ± Standard deviation |
|---|---|---|
| Before WO 87/02248 | 46.2 | 32.1 |
| After 3 months | 37.4 | 30.9 |
| After 6 months | 32.9 | 26.4 |
| After 9 months | 29.4 | 21.8 |
| After 12 months | 27.9 | 21.3 |

Care has to be taken in this case that the patients in both groups investigated here have additionally received a long-term basic therapy which has already been carried out for a long time at the beginning of the test. This was not changed, as the discovery was unforeseeable. The effects as a result of the medicament on a plant basis according to WO 87/02248 consequently go beyond effects already achieved. In this case, the group of the medicaments on a plant basis according to WO 87/02248 starts out from more unfavourable values than the placebo group.

Under these conditions, a reduction in the erythrocyte sedimentation test of 31% is a considerable effect.

During monitoring of 5 patients with rheumatoid arthritis who had already been treated, it turned out that as a result of additional administration of the medicament on a plant basis according to WO 87/02248, downward changes, i.e. in the therapeutic direction, occur (lacuna) the starting values in three out of five cases in the erythrocyte sedimentation test and in four out of five cases with C-reactive protein within four weeks. This clear effect is surprising for several reasons:

1. The dosages used here have not been determined with respect to the basic therapeutic activity. They correspond, rather, to the dose on symptomatic therapy.
2. The effects observed are additional effects in the basic therapy already carried out. In the case of the discovery, it would be ethically unjustifiable to withhold a known effective therapy from the seriously ill. It was completely unexpected that a further increase in the basic therapeutic activity could occur over and above this traditional therapy.
3. For the appreciation of the discovery, it has to be considered that the medicament on a plant basis according to WO 87/02248 is essentially better tolerated compared to other antirheumatics. From this, there is the possibility
   3.1 both to achieve greater effects by means of higher doses and
   3.2 to increase their effectiveness further by additional use of the medicament according to WO 87/02248 in addition to traditional basic therapy.

We claim:

1. A method of treating systemic inflammation caused by inflammatory rheumatic disease in a patient in need of such treatment wherein a change in the course of the inflammatory rheumatic disease occurs as a result of the treatment, comprising reducing or avoiding joint destruction and reducing C-reactive protein values (CRP) by administering to the patient an anti-inflammatory effective amount of a basic therapeutic, or disease modifying drug comprising aqueous ethanolic extracts of *Populus tremula*, *Solidago virgaurea* and *Fraxinus excelsior* as the active ingredients.

2. The method according to claim 1, wherein said basic therapeutic or disease modifying drug contains about 50–70% by volume *Populus tremula*, 10–30% by volume *Solidago virgaurea* and 10–30% by volume *Fraxinus excelsior*.

3. The method according to claim 1, wherein said basic therapeutic or disease modifying drug contains about 60% by volume *Populus tremula*, 20% by volume *Solidago virgaurea* and 20% by volume *Fraxinus excelsior*.

4. The method according to claim 1, wherein said extract of *Populus tremula* is prepared from the bark and leaves.

5. The method according to claim 4, wherein said bark and leaves of said *Populus tremula* are present in the ratio 1:2.

6. The method according to claim 1, wherein said extract of *Solidago virgaurea* is prepared from the bark and leaves.

7. The method according to claim 6, wherein said bark and leaves of said *Solidago Virgaurea* are present in the ratio 1:2.

8. The method according to claim 1, wherein said extract of *Fraxinus excelsior* is prepared from the bark and leaves.

9. The method according to claim 8, wherein said bark and leaves of said *Fraxinus excelsior* are present in the ratio 1:2.

10. The method according to claim 1 wherein erythrocyte sedimentation test values are reduced.

11. The method according to claim 1 wherein said treatment results in an improvement in the signs of systemic inflammation.

* * * * *

UNITED STATES PATENT AND TRADEMARK OFFICE
CERTIFICATE OF CORRECTION

PATENT NO. : 5,376,372

DATED : December 27, 1994

INVENTOR(S) : OKPANYI et al.

It is certified that error appears in the above-identified patent and that said Letters Patent is hereby corrected as shown below:

Title page, [54], delete "REDUCING" and substitute therefor --INHIBITING--;

[30], please insert --Jul. 9, 1990 [EP] European Pat. Off. ....... PCT/EP90/01114--.

Signed and Sealed this

Thirty-first Day of October 1995

Attest:

BRUCE LEHMAN

Attesting Officer      Commissioner of Patents and Trademarks